United States Patent
Wagner et al.

(10) Patent No.: US 6,350,076 B1
(45) Date of Patent: Feb. 26, 2002

(54) BALL-AND-SOCKET JOINT CONNECTION

(75) Inventors: Carl-Sebastian Wagner, Bretten; Manfred Boebel, Bauschlott, both of (DE)

(73) Assignee: Richard Wolf GmbH, Knittlingen (*) Notice: Subject to any disclaimer, the term of this patent is extended or adjusted under 35 U.S.C. 154(b) by 0 days.

(21) Appl. No.: 09/538,652

(22) Filed: Mar. 30, 2000

(30) Foreign Application Priority Data

May 10, 1999 (DE) .......................... 199 21 576

(51) Int. Cl.$^7$ ................................. F16C 11/00
(52) U.S. Cl. ................... 403/135; 439/38; 439/39; 439/40; 403/56; 403/321; 403/122
(58) Field of Search ............... 439/38, 39, 40; 403/56, 321, 122, DIG. 1, 135; 248/179.1, 181.1, 181.2, 288.31

(56) References Cited

U.S. PATENT DOCUMENTS

| | | |
|---|---|---|
| 3,858,578 A | 1/1975 | Milo |
| 4,491,435 A | 1/1985 | Meier |
| 4,807,618 A | 2/1989 | Auchinleck et al. |
| 5,052,844 A | 10/1991 | Kendall |
| 5,348,259 A * | 9/1994 | Blanco et al. ........ 403/56 |

FOREIGN PATENT DOCUMENTS

| | | |
|---|---|---|
| DE | 27 00 661 | 8/1977 |
| DE | 27 17 828 | 10/1978 |
| DE | 4128641 A1 * | 3/1993 |
| DE | 29521305 U1 * | 1/1997 |
| DE | 196 25 729 A1 | 1/1998 |
| EP | 293 760 B1 | 12/1988 |
| EP | 486 999 A2 | 5/1992 |
| FR | 2660714 A1 * | 10/1991 |

* cited by examiner

Primary Examiner—Lynne H. Browne
Assistant Examiner—Aaron Dunwoody
(74) Attorney, Agent, or Firm—Cohen, Pontani, Lieberman & Pavane

(57) ABSTRACT

Disclosed is a ball-and-socket joint connection, in particular for a holding arm system for holding surgical instruments, with a joint ball sitting in a seat of a joint casing and permitting rotation in several axes and with a ball-shaped joint socket which can be axially displaced to and from the joint ball in a cylindrical section of the joint casing. A magnet is provided which produces a magnetic force between the joint ball and the joint socket such that they are drawn to one another. An actuation element is provided for displacing the joint socket and with this the joint ball is fixable in the seat of the joint casing by way of retracting the joint socket, wherein the joint ball by way of the magnet force is pressed into the seat of the joint casing, and wherein the joint ball by displacing forwards the joint socket with the actuation element is separable from the seat.

13 Claims, 5 Drawing Sheets

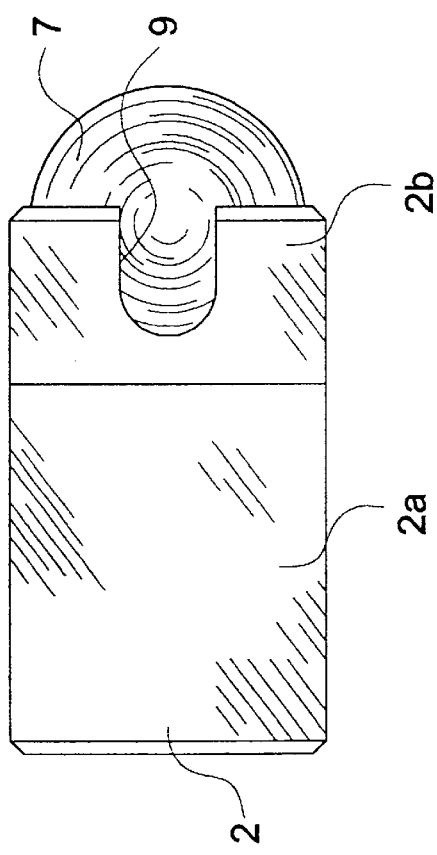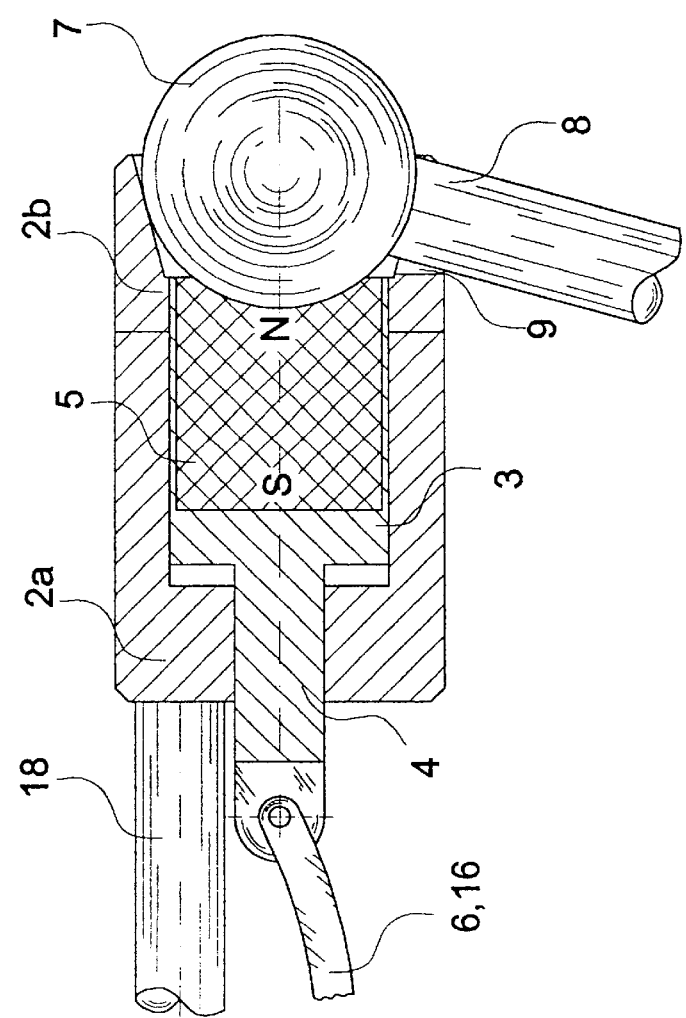

BALL-AND-SOCKET JOINT CONNECTION

BACKGROUND OF THE INVENTION

The invention relates to a ball-and-socket joint connection and, in particular, is for a holding arm system for holding surgical instruments, with a joint ball sitting in a seat of a joint casing and permitting rotations in several axes and with a ball-shaped joint socket which can be axially displaced to and from the joint ball in a cylindrical section of the joint casing, as well as to a holding arm segment using this joint connection.

Within the framework of ergonomic analyses of the operating system "Operating theater for minimal-invasive surgery" in particular with the assisting operator, there has been shown to be a large quantity of burdening static holding work. This results primarily from the absence or the deficient design of suitable auxiliary devices for performing the static hand work. For example, endoscope optics equipped with video cameras are guided by the assistant directed by the operator and for a large period of time during the duration of the operation are held as still as possible. The on-set of fatigue from holding the endoscope optics lead to an inadvertent wandering and to the shaking of the endoscope picture. Similarly this also applies to the holding of organ parts with the help of forceps or wound hooks which with lengthy static holding work with holding forces of more than 15% of the muscle force act in a tiring and ability-reducing manner. Useful holding arm systems which are equipped with suitably designed joint connections may be a solution to this problem.

DE 295 21 305 shows the above mentioned ball-and-socket joint connection for fixing the joint ball in a joint casing using a pressing plate which is actuated by a magneto-restrictive actuator element. If an electrical voltage is applied to the magneto-restrictive element of the actuator this extends and presses, by way of the pressing plate, the joint ball against a conical seat formed in the joint casing. Accordingly, the friction forces acting between the pressing plate, the joint ball and its seat and thus the moment which may be transmitted by the ball-and-socket joint are increased. In this manner an active fixing of the ball-and-socket joint connection may be achieved. In reverse the ball-and-socket joint connection is again released in that the voltage to the magneto-restrictive element of the actuator is switched off.

Although this ball-and-socket joint connection has fulfilled its objects within the framework of the mentioned applications in the operating theater, it has the disadvantage that the individual parts of the ball-and-socket joint connection are not separable from one another, which makes its cleaning and preparation more difficult. Furthermore, the known ball-and-socket joint connection is very complicated and thus comparatively expensive because of the type of actuators equipped with magneto-restrictive elements and because in each case electrical voltages must be applied to these actuators, wherein these voltages must individually be able to be switched on and off. It is therefore rarely applied to simple holding arm systems for holding, for example, forceps systems or wound hook systems

SUMMARY OF THE INVENTION

It is the object of the invention to provide a ball-and-socket joint connection which permits rotation in several axes, allows jerk-free movements, can be fixed and again released in a fine-touch manner by way of a simple operating mechanism and which may be completely separated in a simple manner.

A ball-and-socket joint connection achieving the above object according to an essential aspect of the invention has a magnet which produces a magnetic force between the joint ball and the joint socket such that they are drawn to one another. The ball-and-socket joint of the invention has an actuation element for displacing the joint socket, wherein the joint ball is fixable in the seat of the joint casing by way of retracting the joint socket and with this the joint ball by way of the magnet force is pressed into the seat of the joint casing, and the joint ball by displacing forwards the joint socket with the actuation element is separable from the seat.

In a preferred embodiment of the invention, a spring element exerts a pretensioning force on the joint socket in the direction of its retracted position, wherein the joint socket by way of actuation of the actuation element is displaceable against the pretensioning force of the spring element.

In this manner the ball-and-socket joint connection according to the invention may be released with one hand and the parts may either be changed in their position or separated from one another. In reverse, on account of the pretensioning force brought about by the spring element, the locking of the ball-and-socket joint connection also may be carried out with one hand.

In another preferred embodiment the seat of the joint casing is provided with a shallow cone so that the joint ball in the retracted position of the joint socket comes to lie on the cone surface of the seat. The more shallow the cone, the greater the normal force exerted by the ball surface onto the cone-shaped seat by way of the magnetic force. The holding force is also greater in dependence on the friction coefficients. With steel the cone angle is preferably less than 7°.

The fixing of the joint ball in its seat may also be achieved in that the joint ball is completely or partly elastically deformable. Due to the deformation forces transmitted by the magnet force from the joint socket and the seat to the joint ball, the ball is elastically deformed and is thus no longer movable in its seat.

A further solution to obtain a secure locking of the joint ball in its seat is to provide a uniform grid on the surface of the joint ball and a fitting counter pattern on the seat of the joint casing. For example, the grid of the joint ball is designed in the manner of a golf ball. Accordingly, the grid of the joint ball engages with a positive fit with the counter pattern on the seat of the joint casing in the locked position. The joint ball bears on the seat and is held securely in this position.

The magnetic force may either be produced in that the joint socket itself is formed as an electromagnet or permanent magnet or contains such. Alternatively, the joint ball is either formed as a permanent magnet or contains such or also an electromagnet.

Due to the open formation of the joint casing with the shallow cone, the joint ball in the released condition of the ball-and-socket joint connection may be simply removed from the joint casing.

In a holding arm system according to the invention on one end of a rod-shaped arm there is provided such a ball-and-socket joint connection according to the invention. Alternatively, each of both ends of a holding arm may be provided with such a ball-and-socket joint connection.

For the axial displacement of the joint socket to each individual ball-and-socket joint connection of such a holding arm segment there may be allocated a suitable actuation element.

In another embodiment, the actuation element is in the form of a curved bow which protrudes in the direction of the rod-shaped arm and is pivotably movable on an axial extension of the joint socket, this extension projecting through a bore in the base part of the joint casing. If on both ends of a rigid arm there is fixed a ball-and-socket joint connection according to the invention, the curved actuation bow itself may form the spring element in that it is elastically formed and in the tensioned condition is pivotingly movably applied between the two extensions, pointing to one another, of the joint sockets of the ball-and-socket joint connections on both ends of the holding arm.

The handling of a holding arm system consisting of any number of individual holding arm parts is relatively simple on account of the ball-and-socket joint connection according to the invention and a holding arm segment equipped with this since, for adjusting the respective holding arm segment, only the bow-shaped actuation element engaging on both ball-and-socket joint connections lying opposite one another on the holding arm need be actuated in that it is pressed towards the holding arm against the spring force.

Accordingly, the two joint sockets arranged piston-like in the joint casing are in each case displaced axially in the direction towards the joint ball, by which means these are equally pushed out of the seat of the joint casing by a certain distance. On account of this displacement, the friction between the seat and the joint ball is removed and allows for an easy adjustability of the holding arm.

If on the other hand the pressure force acting on the bow-shaped actuation element is reduced this on account of its elasticity returns to its initial position. Simultaneously the two joint sockets are pulled into the joint casing along with the joint balls. The renewed bearing of each joint ball on the conically formed seat on account of the high friction between the seat and the joint ball as well on account of the high magnet force has the effect that the respective holding arm parts are again brought into an unadjustable or difficultly adjustable position to one another.

The above discussed possible separation by way of the forward displacement of the joint socket against the pretensioning force of the spring element, apart from the advantage of the disassembling into smaller individual pieces and thus of an optimal cleaning and preparation, offers the possibility of combining individual elements, intermediate pieces, branching etc. with one another in any way.

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

FIGS. 5a, 5b show another embodiment of a ball-and-socket joint connection, in which the rod-shaped holding arm part connected to the joint ball may be pivoted in a retrograde manner.

DETAILED DESCRIPTION OF THE PRESENTLY PREFERRED EMBODIMENTS

Figure 1:
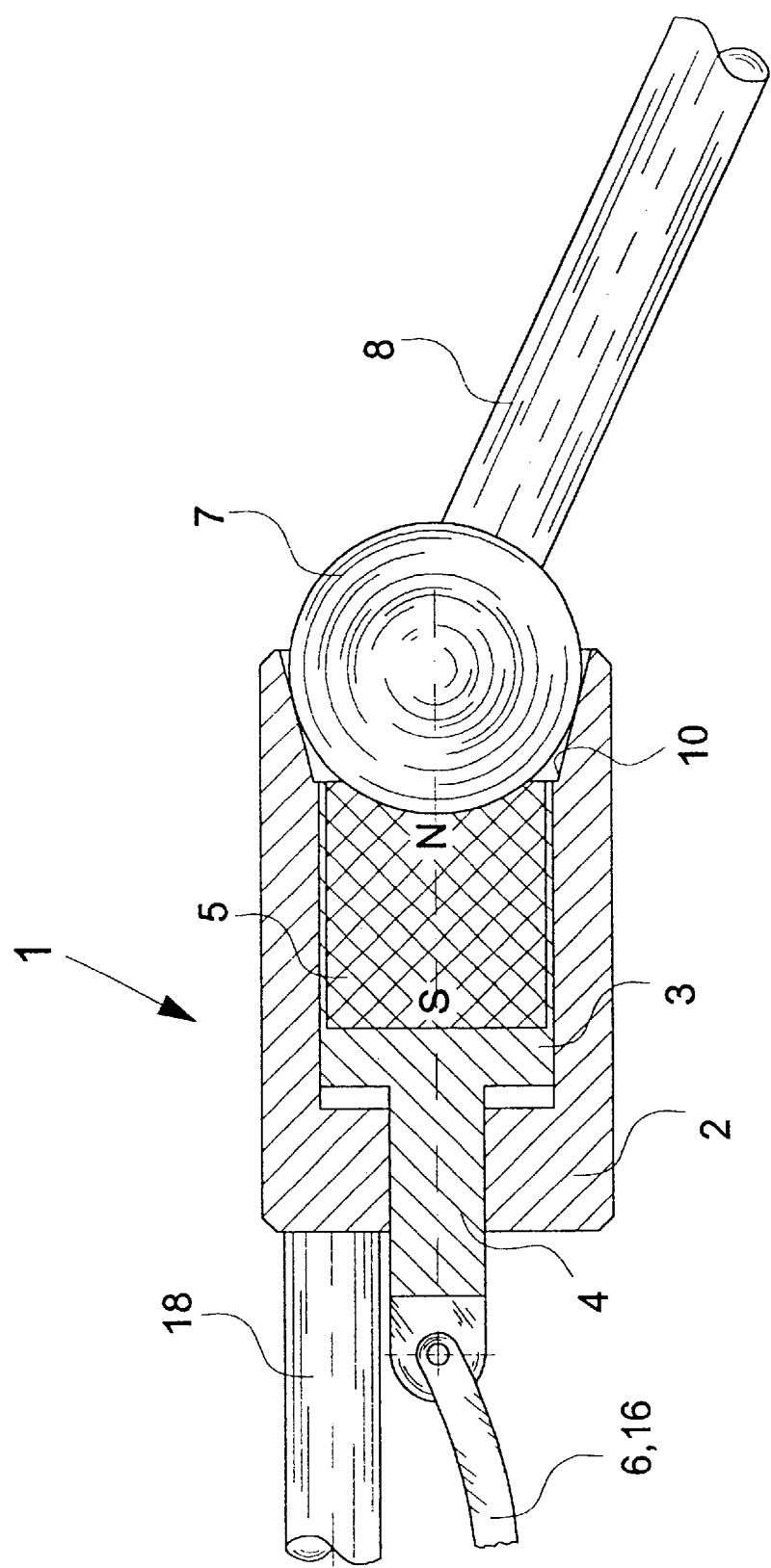
FIG. 1 shows a first embodiment of a ball-and-socket joint connection which connects two holding arm parts to one another.

FIG. 1 shows a first embodiment, indicated generally by reference numeral 1, of a ball-and-socket joint connection according to the invention which on one side is connected to a first holding arm part 8 and on the other side is connected to a second holding arm part 18 and which is equipped for the releasable locking of these two arm parts 8 and 18. The first holding arm part 8 is rigidly fastened to a joint ball 7. The joint ball 7 is seated in a seat 10, and specifically in an annular or annular surface shaped bearing against the seat which is formed conically at one end of an essentially cylindrical joint casing 2. For example, with steel the cone angle of the seat or of the annular surface on which the joint ball 7 is in contact with the seat or the joint casing 2 is preferably less than 7°. Otherwise the whole seat 10 need not have a conical course since it is also sufficient to have only one annular contact surface running conically, and specifically roughly on a step in the space of the joint casing, which otherwise accommodates the remaining joint ball.

The joint casing 2 is at its end facing the conical seat 10 open to the outside. This means that with this open ball-and-socket joint connection the two parts 3 and 7 may be separated from one another and that after removing the magnet force, as explained below, holding the parts together the first holding arm part 8 with the joint ball 7 connected thereto may be removed from the seat 10 of the joint casing 2.

According to FIG. 1 a joint socket formed spherically at its end-face side is axially displaceable within the joint casing 2, i.e. it displaceable towards and away from the joint ball 7. In the joint socket 3 there is provided a permanent magnet or electromagnet 5, and the joint ball 7 is formed ferro magnetically so that a magnetic attraction force is produced between the joint ball 7 and the magnet 5 sitting in the joint socket 3 such that these are pulled towards one another.

The joint socket 3 has at its end opposite to the joint ball 7 an axial extension 4 which projects through a bore mounted in the axial direction on the base of the joint casing 2. At the end of this axial extension 4 there is pivotably mounted a spring-elastic curved actuation bow 6 which is subsequently described.

In the position shown in FIG. 1 the ball-and-socket joint connection is fixed, wherein the friction of the joint ball 7 in the seat 10 formed with a shallow contact surface cone, which is brought about by the force of the magnet 5, is so large that the first arm part 8 connected to the ball 7 on account of this friction force is locked. The ball-and-socket joint connection shown in FIG. 1 is stable on account of the formation and arrangement of the bow-shaped actuation element 6.

For adjusting the holding arm part 8 connected to the joint ball 7 the bow-shaped actuation element 6, which on one side is linkedly connected to the extension 4 of the joint socket 3 accommodating the magnet 5 and on the other side with its (not shown in FIG. 1) oppositely lying end is either rigidly connected to the second holding arm part 18 or likewise linkedly connected to a similar extension 4 of a second such ball-and-socket joint connection, needs only pressed or pivoted in the direction of the second holding arm part 18. Accordingly the joint socket 3 axially displaceable in the joint casing 2 is displaced towards the ball 7, by which means this is likewise displaced by a certain amount out of its seat 10 in the joint casing 2. On account of this displacement the friction between the seat 10 and the ball 7 is removed and by way of this a slight adjustment of the first holding arm part 8 and finally also a complete separation of the ball 7 connected to this holding arm part 8 is made possible.

If the pressure force acting on the actuation element 6 formed as a rod spring 16 is removed, this returns elastically into the initial position shown in FIG. 1. Simultaneously the joint socket 3 and by way of the effect of the magnet 5 also the ball 7 is pulled into the joint casing 2. The renewed bearing of the ball 7 on the seat 10 formed with a shallow cone on account of the high friction between the seat 10 and the ball 7 as well as on account of the magnet force has the effect that the respective holding arm parts 8 and 18 are again brought into and locked in a position unadjustable to one another.

Figure 2:
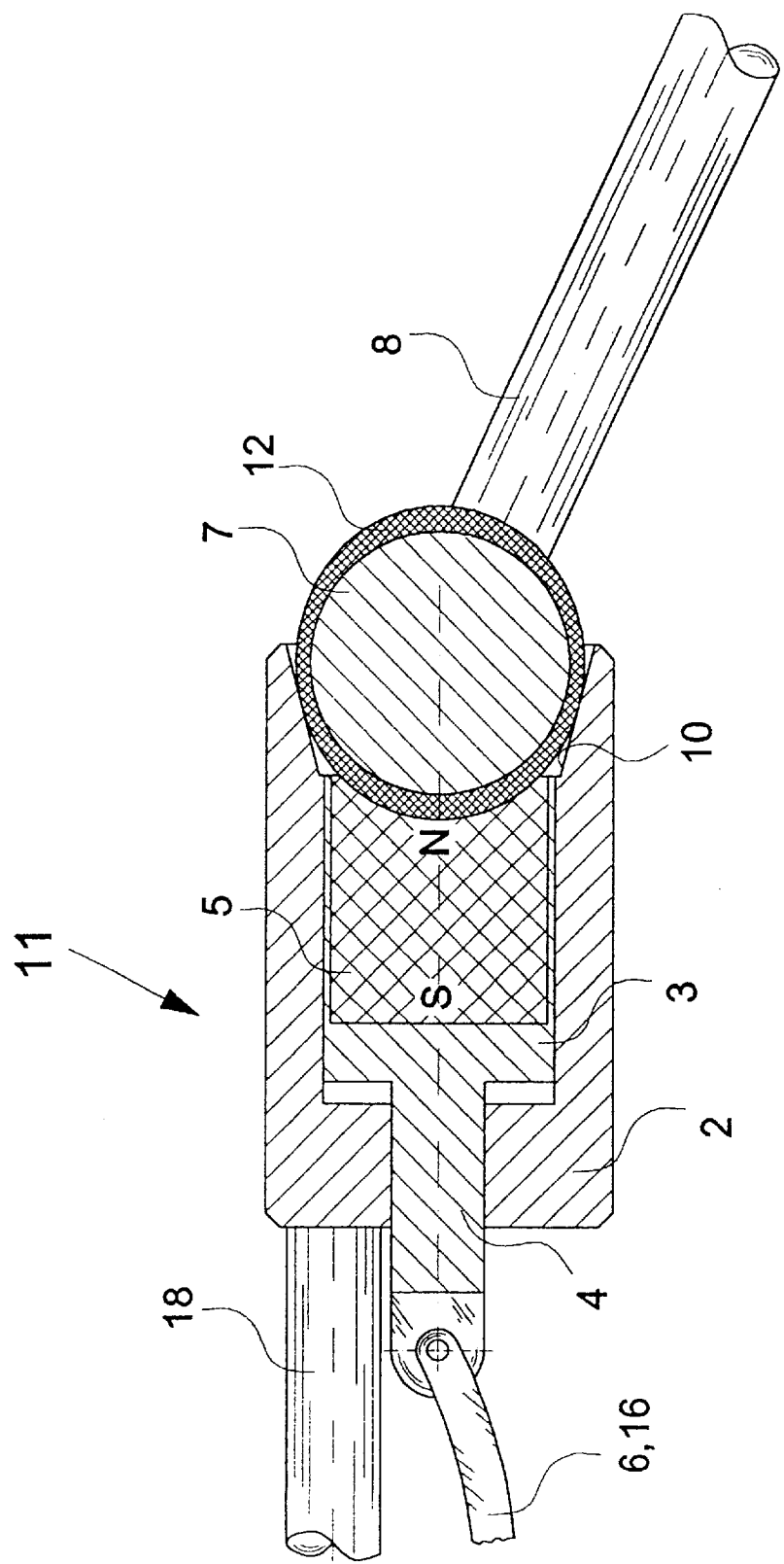
FIG. 2 shows an alternate embodiment of a ball-and-socket joint connection with an elastically designed joint ball.

The schematic representation in FIG. 2 in the same manner as in FIG. 1 shows another embodiment 11 of a ball-and-socket joint connection according to the invention in which the joint ball 7 comprises an elastically deformable casing 12 which may at least deform in the region of the seat 10 of the joint casing 2. Due to the magnetic forces transmitted via the seat 10 of the joint casing 2 onto the ball 7 the elastic casing 12 of the joint ball 7 is deformed and is thus no longer movable in the seat 10.

Figure 3:
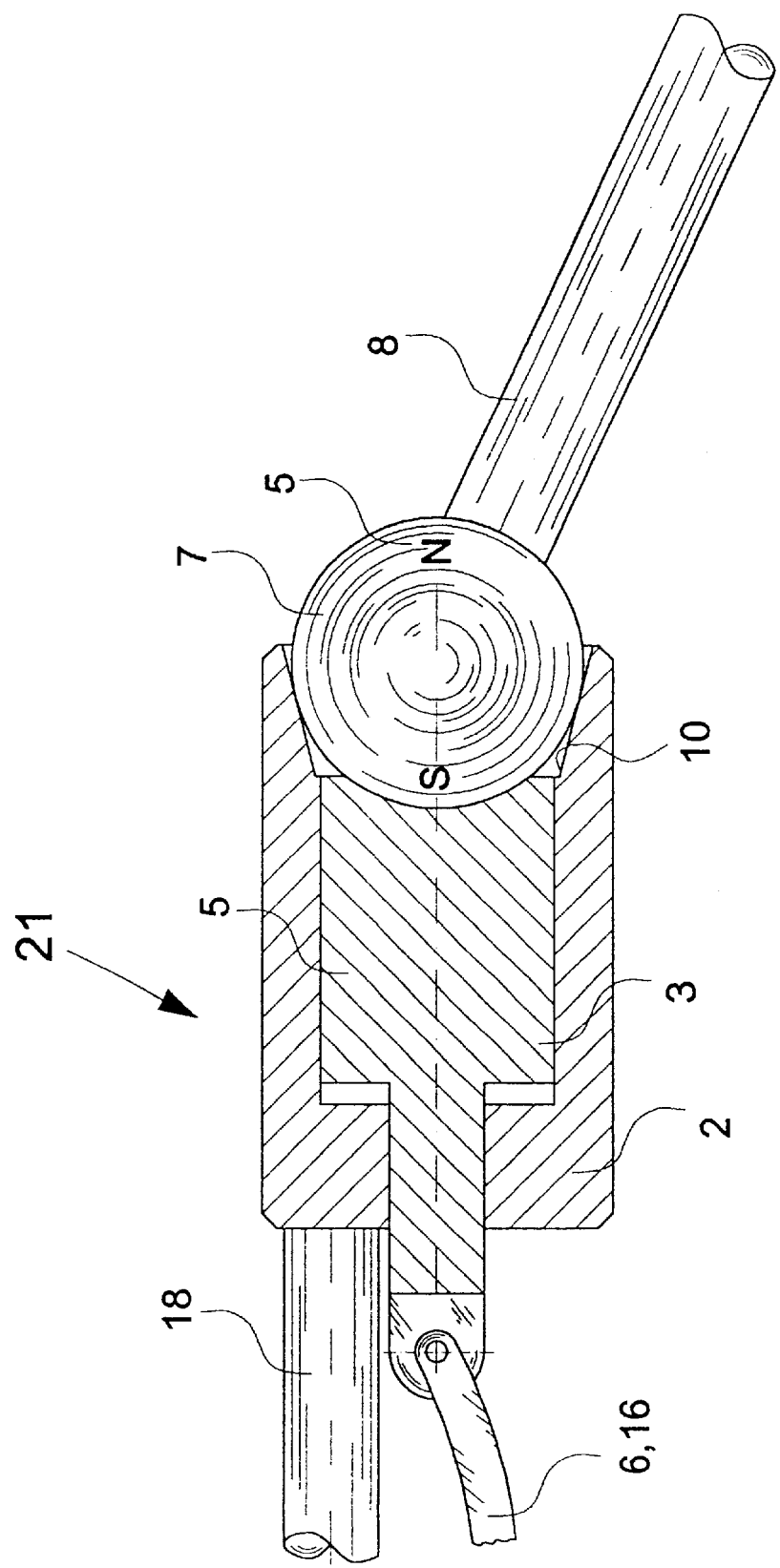
FIG. 3 shows another embodiment of a ball-and-socket joint connection.

FIG. 3 shows schematically a third embodiment form of a ball-and-socket joint connection according to the invention indicated by reference numeral 21, wherein the magnet 5 is not seated in the joint socket 3 as in FIG. 1, but in the joint ball 7. The joint ball 7 is formed as a whole magnetically or only on its surface, wherein then the joint socket 3 at least in the region of the ball-like deepening which bears on the joint ball 7 is formed ferromagnetic. Ball-and-socket joint connection 21 functions as does that of FIG. 1.

In another embodiment of the invention, the joint ball is provided with a uniform surface grid, e.g. as with a football or golf ball. The seat of the joint casing is provided with the fitting counter pattern so that the seat by way of the magnet force may bear on the ball with a positive and secure fit. The increase of the friction value may also be achieved and matched by way of a suitable material selection or material coating or also by way of a surface treatment.

Common to all of the above described embodiments is that by way of a forward displacing of the joint socket 3 effected by the actuation element 16 and by way of the lifting of the joint ball 7 from its seat 10 so effected, the holding arm part 8 connected to the ball 7 may be easily separated from the remaining part of the ball-and-socket joint connection, i.e. that the individual parts may then be differently combined, cleaned and prepared.

Figure 4:
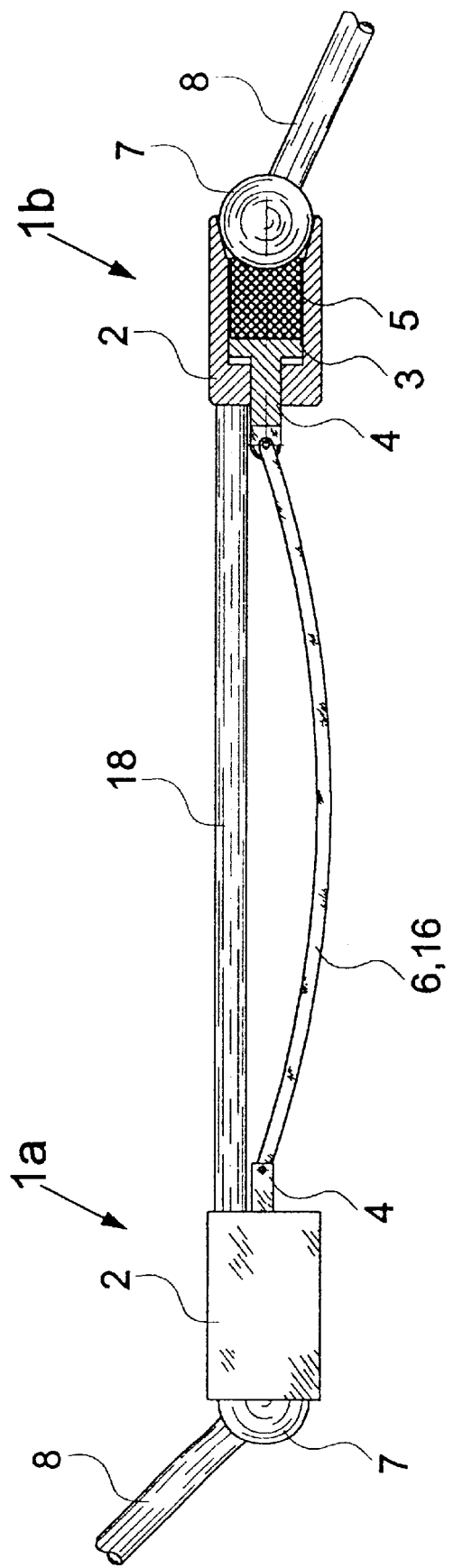
FIG. 4 illustrates a holding arm segment, wherein at both ends of a rigid holding arm, a ball-and-socket joint connection is fixed.

FIG. 4 illustrates a single holding arm segment. A ball-and-socket joint connection according to the invention 1a and 1b, e.g. according to FIG. 1 is rigidly attached at each of both ends of a rod-shaped holding arm 18. The elastic bow-shaped actuation element 6 with the represented locked condition of the ball-and-socket joint connections 1a and 1b lies arch-shaped between the two axial extensions 4 pointing to one another, of the joint socket 3 and here is, in each case, pivotingly movably fastened. On account of its elasticity, the bow-shaped actuation element 6 itself forms the spring element 16.

For adjusting the respective holding arm part 8 connected to the joint ball 7 the bow-shaped actuation element 6 is merely pivoted or pressed in the direction towards the holding arm 18. Accordingly, the joint socket 3 axially movable in the joint casings 2 are in each case displaced in the direction towards the joint balls 7, by which means these are likewise displaced by a certain amount out of the joint casing 2 and are removed from their seat. On account of this displacement the friction between the seat 10 and the joint ball 7 is removed by which means a simple adjustability of the holding arms or holding arm parts 8 and 18 which are connected to one another by the two ball-and-socket joint connections 1a and 1b is made possible.

If the pressure force acting on the actuation element 6 is removed, this element returns into its initial position represented in FIG. 4. Simultaneously the two ball-and-socket joint sockets 3 are in each case pulled into the joint casings 2 taking with them at the same time the joint balls 7. The renewed bearing of the joint balls 7 on the seat 10 which is conically formed in the joint casing 2 in the region of the bearing of the joint ball 7, on account of the high friction between the seat and the ball as well as on account of the magnet force, has the effect that the respective holding arm parts 8 and 18 are again brought into a locked position to one another.

For the axial displacement of the ball-and-socket joint sockets 3 also to each individual joint casing 2 there may be allocated a suitable actuation element, wherein other actuation elements than the spring-elastic bow 6 shown in FIG. 4 are possible.

Finally FIGS. 5a and 5b show a further embodiment of a ball-and-socket joint connection by which a certain disadvantage of the previously described embodiments is eliminated, this disadvantage being in the fact that the rod-shaped holding arm part 8 fastened to the joint ball may not be pivoted in a retrograde manner. According to FIGS. 5a and 5b this problem is solved in that in the joint casing 2 in the region of the joint ball 7 laterally there is mounted a recess 9 accommodating the rod-shaped holding arm part 8. The holding arm part 8 can now be pivoted into this recess, as is represented in FIG. 5b.

The joint casing 2 may comprise a section 2a rigidly connected to the holding arm part 18 and a second section 2b rotatable with respect to the section 2a. Accordingly, the retrogradely pivoted holding arm part 8 can be rotated about any angle. In all other details the embodiment example shown in the FIGS. 5a and 5b may correspond to one of the previously mentioned embodiment examples.

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

We claim:

1. A ball-and-socket joint connection comprising:
   a joint casing having a seat adapted to receive a rotatable joint ball;
   a rotatable joint ball adapted to sit in said seat;
   a joint socket housed in said joint casing and axially displaceable from said joint ball;
   a magnet to produce a magnetic force between the joint ball and the joint socket so as to draw the ball and socket towards one another;
   an actuation element for displacing said joint socket with said joint ball wherein said joint ball is fixable in the seat of the joint casing by way of retracting the joint socket and the joint ball is pressed into the seat of the joint casing, and wherein by displacing forwards the joint socket with the actuation element the joint ball is separable from the seat.

2. The ball-and-socket joint connection of claim 1, further comprising a spring element which exerts a pretensioning force onto the joint socket in the direction of its retracted position and, wherein the joint socket by way of actuation of the actuation element is displaceable against the pretensioning force of the spring element.

3. The ball-and-socket joint connection of claim 1, wherein the seat of the joint socket is formed conically.

4. The ball-and-socket joint connection of claim 1, wherein the joint ball is at least partly elastically deformable and the joint ball at least in the region of the seat deforms when it is pressed onto the seat by the magnet force.

5. The ball-and-socket joint of claim 1, wherein the joint socket has a magnet and the joint ball is formed ferro magnetically.

6. The ball-and-socket joint connection of claim 1, wherein the joint ball has a magnet and the joint socket is formed ferro magnetically.

7. The ball-and-socket joint connection of claim 1, wherein the joint casing is open to the outside and the joint ball is separable, against the magnet force, from the joint casing.

8. The ball-and-socket joint connection of claim 1, wherein the joint ball is rigidly connected to a holding arm.

9. The ball-and-socket joint connection of claim 8, wherein the joint casing is rigidly connected to the holding arm.

10. A holding arm segment for a holding arm system, comprising: a rod-shaped arm having at least one end; and on said least one end of said rod-shaped arm a ball-and-socket joint connection is rigidly fixed, said ball-and-socket joint connection comprising a joint casing having a seat adapted to receive a rotatable joint ball;

a rotatable joint ball adapted to sit in said seat;

a joint socket housed in said joint casing and axially displaceable from said joint ball;

a magnet to produce a magnetic force between the joint ball and the joint socket so as to draw the ball and socket towards one another;

an actuation element for displacing said joint socket with said joint ball wherein said joint ball is fixable in the seat of the joint casing by way of retracting the joint socket and the joint ball is pressed into the seat of the joint casing, and wherein by displacing forwards the joint socket with the actuation element the joint ball is separable from the seat.

11. The holding arm segment of claim 10, wherein the actuation element is a rod-shaped how which is pivotingly movably connected to an axial extension of the axially displaceable joint socket and which essentially projects in the direction of the rod-shaped arm, and wherein the extension projects through a bore provided in the axial direction into a base wall of the joint casing lying opposite the joint ball.

12. The holding arm segment of claim 11, wherein the bow is spring-elastic and is applied arch-shaped between the extension and the other end of the rod-shaped arm and forms the spring element.

13. The holding arm segment of claim 12, wherein the curved bow forming the spring element is applied between the extensions of the two joint sockets of the ball-and-socket joint connection at the two ends of the rod-shaped arm.

* * * * *